United States Patent
Gluck et al.

(10) Patent No.: US 7,163,914 B2
(45) Date of Patent: *Jan. 16, 2007

(54) ALKYLPOLYGLUCOSIDES CONTAINING DISINFECTANT COMPOSITIONS ACTIVE AGAINST PSEUDOMONAS MICROORGANISM

(75) Inventors: Bruno Anthony Gluck, North Gosford (AU); Hyo Sang Kwon, Rosebery (AU)

(73) Assignee: Novapharm Research (Australia) Pty. Ltd., Rosebery (AU)

( * ) Notice: Subject to any disclaimer, the term of this patent is extended or adjusted under 35 U.S.C. 154(b) by 268 days.

This patent is subject to a terminal disclaimer.

(21) Appl. No.: 10/372,663

(22) Filed: Feb. 25, 2003
(Under 37 CFR 1.47)

(65) Prior Publication Data

US 2005/0215461 A1 Sep. 29, 2005

Related U.S. Application Data

(63) Continuation-in-part of application No. 09/424,158, filed as application No. PCT/AU98/00329 on May 7, 1998, now Pat. No. 6,531,434.

(30) Foreign Application Priority Data

May 20, 1997 (AU) .................................... PO6909

(51) Int. Cl.
C11D 9/50 (2006.01)
C11D 3/22 (2006.01)
C11D 3/44 (2006.01)
C11D 3/48 (2006.01)

(52) U.S. Cl. ............ 510/131; 510/130; 510/151; 510/199; 510/319; 510/382; 510/386; 510/470; 510/475; 422/28; 422/37; 424/404

(58) Field of Classification Search ........ 510/130, 510/131, 151, 199, 319, 382, 386, 470, 475; 422/28, 37; 424/404
See application file for complete search history.

(56) References Cited

U.S. PATENT DOCUMENTS

| | | | |
|---|---|---|---|
| 5,164,107 A | 11/1992 | Khan et al. | |
| 5,409,697 A | 4/1995 | Gluck | |
| 5,624,906 A | 4/1997 | Vermeer | |
| 5,646,100 A | 7/1997 | Haugk et al. | |
| 5,691,287 A | 11/1997 | Villars et al. | |
| 5,719,113 A | 2/1998 | Fendler et al. | |
| 5,762,917 A | 6/1998 | Osborne | |
| 5,763,412 A | 6/1998 | Khan et al. | |
| 5,888,520 A | 3/1999 | Toma et al. | |
| 5,922,313 A | 7/1999 | Steward et al. | |
| 6,008,246 A | 12/1999 | Ito et al. | |
| 6,037,386 A | 3/2000 | Modak et al. | |
| 6,045,817 A | 4/2000 | Ananthapadmanabhan et al. | |
| 6,531,434 B1 * | 3/2003 | Gluck ................ | 510/131 |

FOREIGN PATENT DOCUMENTS

| | | |
|---|---|---|
| AU | 11662/95 | 8/1995 |
| EP | 0 670 158 A2 | 9/1995 |
| JP | 61-140508 | 6/1986 |
| JP | 01-144497 | 6/1989 |
| JP | 07-539995 | 2/1995 |
| JP | 08-501122 | 2/1996 |
| JP | 08199188 | 8/1996 |
| JP | 10-549693 | 12/2001 |
| WO | WO 86/05359 | 9/1986 |
| WO | WO 89/00006 | 1/1989 |
| WO | WO 92/13055 | 8/1992 |
| WO | WO 93/07250 | 4/1993 |
| WO | WO 95/09605 | 4/1995 |
| WO | WO 97/48377 | 12/1997 |

OTHER PUBLICATIONS

"Gendai Biseibutsu-gaku" (Comptempory Microbiology), 3$^{rd}$ de., (Asakura Shoten, Apr. 15, 1994), pp. 232-235 and colophon.
"Koushouhin Iyakuhin Bouhu-Sakkinzaino Kagaku" (Science of cosmetics, pharmaceuticals, antiseptics, and bactericides), (Fragrance Journal Ltd., 1984), front cover, table of contents (3 pages), pp. 63-88 and 516-517.
"Senzai Senjou-no-jiten" (encyclopedia of detergents and cleaning), (Asakura Shoten, Nov. 25, 1990), pp. 92-93.

* cited by examiner

Primary Examiner—Brian P Mruk
(74) Attorney, Agent, or Firm—Venable LLP; James R. Burdett; Keith G. Haddaway

(57) ABSTRACT

An antiseptic cleansing composition comprising an antimicrobial agent, an effective amount of an alkylpolysaccharide surfactant, at least one alkyl alcohol and at least one aryl alcohol. Suitable surfactant alkylpolysaccharides may contain one or more sugar units selected from the group consisting of maltose, arabinose, xylose, mannose, galactose, gulose, idose, talose, allose, altrose, sucrose, fructose, sorbose, levulose, lactose, allulose, tagatose, alloheptulose, sedoheptulose, glucoheptulose, mannoheptulose, guloheptulose, idoheptulose, galactoheptulose, taloheptulose and derivatives thereof. Suitable antimicrobial agents include chlorhexidine, chlorhexidine salt, chlorophenol derivative, octenidindihydrochloride ($CH_3$—$(CH_2)_7$—NHON—$(CH_2)_{10}$—NO—NH$(CH_2)_7$—$CH_2$ or any other salt thereof, and quaternary ammonium compounds.

36 Claims, No Drawings

ALKYLPOLYGLUCOSIDES CONTAINING DISINFECTANT COMPOSITIONS ACTIVE AGAINST PSEUDOMONAS MICROORGANISM

CROSS REFERENCE TO RELATED APPLICATIONS

This application is a continuation-in-part of application Ser. No. 09/424,158, filed Mar. 23, 2000 now U.S. Pat. No. 6,531,434, which is the National Stage of International Application No. PCT/AU98/00329, filed May 7, 1998 which claims the benefit of Australian application No. PO 6909 filed May 20, 1997, each of which is incorporated by reference herein in its entirety.

TECHNICAL FIELD

This invention relates to a disinfectant cleansing composition.

BACKGROUND OF THE INVENTION

It is known that infection is spread via skin contact through the transmission of pathogenic microorganisms. Hitherto, in order to reduce the presence of such organisms it has been known to scrub the skin with a solution containing a surfactant followed by application of an antiseptic.

In recent years it has been suggested that it would be desirable to combine the washing and disinfectant actions in a single operation by providing a composition comprising both an antimicrobial agent and a surfactant. It has been found however that many antimicrobial agents such as chlorhexidine [N,N'-bis(4-chlorophenyl)-3,12-diimino 2,4,11,13-tetraazatetradecanediimidamide] digluconate and other chlorhexidine salts are incompatible with anionic surfactants, and are reduced in their antimicrobial activity by nonionic surfactants, thus requiring addition of more antimicrobial agent in order to retain sufficient biocidal activity at the amount of surfactant required for satisfactory foam formation.

In particular, U.S. Pat. No. 3,855,140 assigned to Imperial Chemical Industries describes a skin cleansing composition comprising a soluble salt of chlorhexidine in combination with a polyoxyethylenepolyoxypropylene block copolymer. In order to obtain sufficient sudsing of the polymer it is necessary to use high proportions of the surfactant in amounts of the order of 20–25%. High amounts of chlorhexidine are consequently required to maintain the desired antimicrobial activity. Such high amounts are undesirable as it is known that surfactants may affect the skin adversely by defatting, and causing, when in combination with biocides such as chlorhexidine, irritation to the skin. Further the ingredients of the composition can be costly.

It would be desirable therefore to provide a composition in which the amount of antimicrobial agent and surfactant is reduced whilst maintaining sufficient antimicrobial activity and sudsing ability.

In this regard, in order to provide such a composition, WO 95/09605 teaches one to combine a phenolic disinfectant with an alkylpolyglucoside surfactant. As indicated in that patent however, such compositions, although showing good biocidal activity against most microorganisms, are incapable of disinfecting surfaces contaminated by the microorganism Pseudomonas aeruginosa to which the compositions are inactive.

It is an object of the invention to substantially ameliorate the disadvantages of the prior art.

DESCRIPTION OF THE INVENTION

According to a first aspect of the invention, there is provided an antiseptic cleansing composition comprising an antimicrobial agent, an effective amount of an alkylpolysaccharide surfactant, at least one alkyl alcohol and at least one aryl alcohol.

According to a second aspect of the invention there is provided a method of decontaminating surfaces contaminated with bacteria including the Pseudomonas microorganism, which method comprises contacting the surface with the disinfectant cleansing composition of the first aspect.

Typically the cleansing composition comprises an inert carrier, and optionally other additives.

The alkylpolysaccharide surfactants are also known in the art as alkylpolyglucosides. However, for the purposes of the following discussion, the surfactant will be termed an alkylpolysaccharide.

Preferably, the content of the surfactant present in the composition does not exceed 6% w/v.

Preferably the alkylpolysaccharide is an alkylpolysaccharide of the formula:

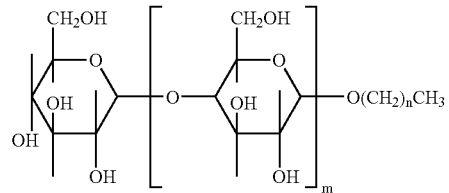

wherein n is an integer between 5 and 19, and m is an integer between 1 and 3.

In the above formula the surfactant alkyl polysaccharide shown contains glucose units, however the invention is not limited thereto and other sugar units can be substituted for one or more of the glucose units. Other sugar units which might be included in the alkylpolysaccharide include maltose, arabinose, xylose, mannose, galactose, gulose, idose, talose, allose, altrose, sucrose, fructose, sorbose, levulose, lactose, allulose, tagatose, alloheptulose, sedoheptulose, glucoheptulose, mannoheptulose, guloheptulose, idoheptulose, galactoheptulose, taloheptulose and derivatives thereof.

Suitable antimicrobial agents include chlorhexidine and its salts; dichlorophene, other chlorophenol derivatives such as p-chloro-m-xylenol, chlorophene and o-phenylphenol, 2,4,4-trichloro-2-hydroxy-diphenylether (triclosan); octenidindihydrochloride ($CH_3$—$(CH_2)_7$—NHON—$(CH_2)_{10}$—NO—NH$(CH_2)_7$—$CH_2$ or any other salt thereof and quaternary ammonium compounds.

Suitable salts of chlorhexidine include the gluconate, isethionate, formate, acetate, glutamate, succinamate, monodiglycolate, dimethanesulfonate, lactate, diisobutyrate or the glucoheptonate salts.

Preferably the antimicrobial agent has a water solubility of at least 0.001% w/v at ambient temperature.

When the antimicrobial agent is chlorhexidine digluconate it is used in an amount preferably not exceeding 4.5% w/v. When the antimicrobial agent is 2,4,4-trichloro-2-hydroxydiphenylether (triclosan) it is used in an amount preferably not exceeding 3% w/v.

The alkyl alcohol is preferably a lower alkyl alcohol (herein defined as an alcohol having less than 6 carbon atoms) such as ethanol, iso- or n-propanol, most preferably the alkyl alcohol is isopropanol or n-propanol. The alcohol content preferably does not exceed 70% w/v. When the composition is in an aqueous carrier (for example, for use in hand washing) the alcohol is desirably iso- or n-propanol or a combination thereof and is preferably present in an amount of from 3 to 10% w/v, most preferably 4 to 8% w/v. When the composition is an alcoholic solution (for example for a rapid cleaning self-drying solution) the alkyl alcohol will be preferably be 55–75% w/v.

The aryl alcohol is preferably a benzylalcohol, phenylethylalcohol, phenoxyethanol, phenoxypropanol or a chlorinated derivative thereof. For application to skin, phenoxyethanol and phenoxypropanol are preferred. Preferably the aryl alcohol is present in an amount not exceeding 3% w/v.

An inert carrier can be used—for example water or a lower alcohol such as ethanol.

The composition may further comprise one or more of the following integers:

(a) a solubilising agent, for example, propylene glycol, a hydrotrope or mixtures thereof. Suitable hydrotropes include urea, cumene sulphonate, toluene sulfonate, xylenesulphonate and the ethanolamine salts of citric and other hydroxycarboxylic acids.

(b) a foaming agent, such as an alkylaminooxide, alkylmono or diethanolamides. Examples of foaming agents are lauryl or cocodiethanolamide or monoethanolamide condensates or the lauryl or cetyl dimethylamineoxides.

(c) viscosity modifiers, such as cellulose derivatives, guar resins and carbopol resins.

(d) preservatives, such as imidazolidinyl, urea derivatives (Germabenes), methyl or propyl parabens (p-hydroxy benzoic esters).

(e) other conventional additives, such as coloring agents, fragrances, antioxidants, emolients, moisturisers, stabilising agents and thickeners such as carboxymethylcellulose.

(f) optionally, additional surfactants, including amphoteric surfactants, anionic surfactants and nonionic surfactants. Suitable additional surfactants include quaternary ammonium compounds or a small amount of a high foaming anionic surfactant such as laurylethoxysulfonate, sarcosinates, sodium laurylethersulphate. The additional ingredients are selected to avoid possible incompatibility with any of the other ingredients of the composition and especially with regard to the antimicrobial agents.

The pH of the composition is typically adjusted to pH 5 to 7, most preferably 5.5 but is not limited to this pH. When chlorhexidine is used as the antimicrobial agent, a pH greater than 8 should be avoided to prevent precipitation of the chlorhexidine free base. Most organic acids compatible with the composition, such as lactic, acetic, citric and gluconic acids, preferably gluconic acid, can be used to adjust the pH.

The term "comprising" as herein used is used in an inclusive sense, that is to say in the sense of "including" or "containing". The term is not intended in an exclusive sense ("consisting of" or "composed of").

The following examples illustrate preferred embodiments of the present invention. They should not be construed as limiting.

It will also be understood by those skilled in the art that while the present invention is described herein with reference to a concentrate, such a concentrate could be diluted prior to sale (for example to 55%) or use.

EXAMPLES

Example I

| Comparative composition in accordance with WO 95/09605 | |
|---|---|
| Sodium laurylsulfate (100%) | 4.67% w/v |
| Alkylpolysaccharide (100%) | 3.92% w/v |
| Coconut Betaine (100%) | 0.90% w/v |
| Triclosan | 0.49% w/v |
| Propylene glycol | 0.254% w/v |
| Glycerine | 0.254% w/v |
| Sodium chloride | 0.49% w/v |
| Citric acid | up to 10% w/v |
| Water | to 100% by volume |

Example II

Comparative Commercial Antibacterial Skin Cleanser Containing 2.0% (Triclosan) Full Composition Unknown)

Example III

| Comparative Composition of Commercial Antiseptic Surgical Scrub | |
|---|---|
| Chlorhexidine Gluconate (CHG) | 4.0% w/v |
| Nonionic Surfactant* (100%) | 25.00% w/v |
| Lauryl Dimethylamineoxide (100%) | 2.60% w/v |
| Water | to 100.0% by volume |

(formula as per published data (Manuf. Chemist, October 1973, p. 25–27 and disclosed in U.S. Pat. No. 3 855 140)
*polyoxyethylene/polyoxypropylene block copolymer PLURONIC F87 (BASF, Germany).

Example IV

Inventive Composition containing Triclosan

Same composition as Example 1 to which n-propanol 5.0% w/v and phenoxyethanol 1% w/v have been added.

Example V

Inventive Composition containing Triclosan

Same composition as Example 1 to which 5.0% w/v n-propanol and 1% w/v phenoxyethanol have been added and the triclosan increased to 1% w/v.

Example VI

| Inventive Composition Containing Chlorhexidine Gluconate | |
|---|---|
| Chlorhexidine Gluconate (CHG) | 2.0% w/v |
| Alkylpolysaccharide* (100%) | 4.00% w/v |
| Cocodiethanolamide (100%) | 2.00% w/v |
| Propylene Glycol | 2.0% w/v |
| Isopropanol | 8.0% w/v |
| Phenoxyethanol | 2.0% w/v |
| Water | to 100% by volume |

*Oramix ™ NS10 55% w/v (Sepic SA, France).

Example VII

| Inventive Compositions Containing Chlorhexidine Gluconate | |
|---|---|
| Chlorhexidine gluconate (CHG) | 1.0% w/v |
| Alkylpolysaccharide* (100%) | 4.00% w/v |
| Cocodiethanolamide (100%) | 0.80% w/v |
| Propylene glycol | 2.0% w/v |
| n-propanol | 6.0% w/v |
| Phenoxypropanol | 1.0% w/v |
| Water | to 100.0% by volume |

*Any commercial alkylpolysaccharide can be used such as Plantaren ™ 2000 (Henkel) or Atlas ™ G73500 (ICI).

Example VIII

| Inventive Composition Containing Triclosan | |
|---|---|
| Triclosan | 1.0% w/v |
| Alkylpolysaccharide* (100%) | 4.00% w/v |
| Sodium 2 laurylethersulfate (100%) | 0.20% w/v |
| Cocodiethanolamide (100%) | 2.00% w/v |
| Isopropanol | 8.0% w/v |
| Propylene Glycol | 10.0% w/v |
| Preservative** | 1.0% w/v |
| Phenoxyethanol | 2.0% w/v |
| Water | to 100.0% by volume |

*Oramix ™ NS12 (Sepic SA, France)
**Germabene ™ II 0.2% w/v

Example IX

| Inventive Composition Containing Triclosan | |
|---|---|
| Triclosan | 1.0% w/v |
| Alkyl polysaccharide* (100%) | 4.00% w/v |
| Sodium 2 laurylethersulfate (100%) | 0.25% w/v |
| Sodium cumene sulfate (100%) | 4.00% w/v |
| Ethyl alcohol | 4.0% w/v |
| n-propanol | 4.0% w/v |
| Phenoxyethanol | 1.5% w/v |
| Water | to 100% by volume |

*Any commercial alkylpolysaccharide can be used such as Plantaren ™ 2000 (Henkel) or Atlas ™ G73500 (ICI).

Example X

| Inventive Composition Containing Triclosan | |
|---|---|
| Triclosan | 1.00% w/v |
| Alkylpolysaccharide (100%) | 2.75% w/v |
| Cocodiethanolamide (100%) | 0.80% w/v |
| Sodium xylene sulphonate (100%) | 4.00% w/v |
| Isopropanol | 8.0% w/v |
| Propylene glycol | 2.0% w/v |
| Phenoxyethanol | 1.0% w/v |
| Carboxymethyl cellulose | 0.6% w/v |
| Phenoxypropanol | 1.0% w/v |
| Water | to 100.0 by volume % |

Example XI

| Inventive Composition Containing Dichlorophene | |
|---|---|
| Dichlorophene | 1.5% w/v |
| Alkylpolysaccharide (100%) | 4.00% w/v |
| Sodium 2 laurylethersulfate (100%) | 0.20% w/v |
| Cocodiethanolamide (100%) | 2.00% w/v |
| Isopropanol | 5.0% w/v |
| Phenoxyethanol | 1.0% w/v |
| Water | to make 100.0% by volume |

Example XII

| Inventive Composition Containing Dichlorophene | |
|---|---|
| Dichlorophene | 1.5% w/v |
| Alkylpolysaccharide (100%) | 4.00% w/v |
| Sodium 2 laurylethersulphate (100%) | 0.50% w/v |
| Cocodiethanolamide (100%) | 1.00% w/v |
| Ethanol | 5.0% w/v |
| Phenoxyethanol | 1.0% w/v |
| Water | to make 100.0% by volume | adjust pH to 7.0–7.2 with triethanolamine.

Suspension tests were performed (in accordance with European Standard CEN/TC216/WG IN) in the presence of a number of organisms. The results are shown in the following table:

TABLE I

SUSPENSION TESTS
RESULTS EXPRESSED AS: log reduction
Test temperature: 23° C.; Contact time: 60 seconds
Neutralising Medium: Tween80 100 g/L, Lecithin 50 g/L, Histidine 1 g/L

| TEST ORGANISM: | E. Coli NCTC 8196 | S. aureus NCTC 4163 | P. aeruginosa NCTC 6749 | S. faecalis NCTC 775 |
|---|---|---|---|---|
| Concentration | Neat | Neat | Neat | Neat |
| Contact Time (secs) | 60 | 60 | 60 | 60 |
| Formulations: | | | | |
| Comparative Example I 0.49% w/v Triclosan | NG | NG | >2 | >2 |
| Inventive Example IV 0.49% w/v Triclosan | NG | NG | NG | NG |
| Comparative Example II 2% w/v Triclosan | >2 | >2 | >2 | >2 |

TABLE I-continued

SUSPENSION TESTS
RESULTS EXPRESSED AS: log reduction
Test temperature: 23° C.; Contact time: 60 seconds
Neutralising Medium: Tween80 100 g/L, Lecithin 50 g/L, Histidine 1 g/L

| TEST ORGANISM: | E. Coli NCTC 8196 | S. aureus NCTC 4163 | P. aeruginosa NCTC 6749 | S. faecalis NCTC 775 |
|---|---|---|---|---|
| Inventive Example V 1.0% w/v Triclosan | NG | NG | NG | NG |
| Comparative Example III 2% w/v CHG | NG | 3.8 | NG | 3.9 |
| Inventive Example VI 2.0% w/v CHG | NG | NG | NG | NG |
| Inoculum Level | $2.5 \times 10^8$ | $2.8 \times 10^8$ | $1.3 \times 10^8$ | $1.8 \times 10^8$ |

NG: Means NO GROWTH

Suspension tests were also conducted for the composition of Example X (1.0% w/v Triclosan). The results were as follows:

Microbicidal Results

Suspension test —30 sec contact/con. 75%

Expressed as a Log reduction of microorganisms.

| Microorganism | Inoculum level | Reduction |
|---|---|---|
| S. aureus ATTC 6538 | Log 6.8 | >5.8 |
| E. coli ATTC 11229 | Log 6.9 | >5.9 |
| PS aeruginosa ATTC 15442 | Log 7.0 | >6.0 |
| P. mirabilia ATTC 14153 | Log 6.8 | >6.0 |

Example XIII

| Inventive Compositions Containing Chlorhexidine Gluconate | |
|---|---|
| Ethanol | 55.23 (w/v) (70% v/v) |
| Chlorohexidine digluconate | 0.50 w/v |
| Glycerol | 0.80 w/v |
| Akylpolyglucoside(apg) | 2.10 w/v |
| Benzyl alcohol | 0.55 w/v |
| Peg-75 lanolin | 0.10 w/v |
| Isopropylmyristate(ipm) | 0.05 w/v |
| Fragrance | 0.10 w/v |
| Dyestuff(fd&c red no 33) | 0.00020 w/v |
| Lactic acid (to pH 5.50) | 0.10 w/v (maximum) |
| Triethanolamine (to pH 5.50) | 0.10 w/v (maximum) |
| Water (purified) | to make 100% by volume |

Example XIV

| Inventive Compositions Containing Triclosan | |
|---|---|
| Ethanol | 55.23 w/v (70% v/v) |
| Triclosan | 0.80 w/v |
| Propylene glycol | 1.00 w/v |
| Polyethylene glycol 400 | 1.00 w/v |
| Akylpolyglucoside(apg) | 2.10 w/v |
| Phenoxy ethanol | 0.55 w/v |
| Isopropylmyristate(ipm) | 0.05 w/v |
| Peg-75 lanolin | 0.10 w/v |
| Fragrance | 0.10 w/v |
| Dyestuff(d&c green no 3) | 0.00020 w/v |
| Phosphoric acid (to ph 5.50) | 0.10 (maximum) |
| Triethanolamine(to ph 5.50) | 0.10 (maximum) |
| Water (purified) | to make 100% by volume |

Compositions according to the invention have the same or greater effectiveness with respect to biocidal activity and are less toxic, at much lower concentrations of the antimicrobial agent in comparison with conventional prior art compositions.

In preferred embodiments, the use of an alkylpolysaccharide surfactant in amounts below 6% (w/v), the amount of triclosan can be successfully reduced from 1.0% to 0.5% (w/v) with substantially no loss in biocidal activity. Surprisingly, the amount of chlorhexidine can be reduced 4% to 2% (w/v) whilst maintaining good biocidal activity and foaming properties.

Further, by use of alkylpolysaccharides in amounts as low as 2% it is possible to obtain sufficient foaming skin cleansing properties not obtainable with other conventional surfactants. Further, the known interference with the antimicrobial properties of biocides with surfactants is considerably reduced.

Further, by the inclusion of an alkyl and aryl alcohol combination, the compositions of the invention are effective against the pseudomonas microorganism.

The invention is a significant and important improvement on the art as taught in U.S. Pat. No. 3,855,140 as illustrated by the fact that, while the composition of U.S. Pat. No. 3,855,140 showed no activity against Pseudomonas, the compositions of the present invention are effective against Pseudomonas at concentrations containing as low as 0.49% triclosan.

Compositions according to the invention are especially suitable for skin and hand disinfection, surface disinfection, impregnation of sponges, woven and non-woven textiles and the like.

The composition of the invention is suitable for cleansing any object. The composition of the invention is particularly suitable for cleansing hands in clinical situations and before surgery but can also be used for cleansing inanimate objects such as surgical instruments.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. An antiseptic composition effective for cleansing and disinfecting a surface and effective against Pseudomonas comprising an antimicrobial agent; at least 2% w/v of an alkylpolysaccharide surfactant; at least one alkyl alcohol; and at least one aryl alcohol, wherein the total weight of said alkyl and aryl alcohols is at least 55% w/v of the composition.

2. A composition according to claim 1 wherein the antimicrobial agent is selected from the group consisting of chlorhexidine, chlorhexidine salt, chlorophenol derivative, octenidindihydrochloride $(CH_3-(CH_2)_7-NHON-(CH_2)_{10}-NO-NH(CH_2)_7-CH_2)$- or any other salt thereof, and quaternary ammonium compounds.

3. A composition according to claim 1 wherein the aryl alcohol is selected from the group consisting of phenoxyethanol and phenoxy propanol and chlorinated derivatives thereof.

4. A composition according to claim 1 wherein the alkylpolysaccharide is an alkylpolysaccharide of the formula:

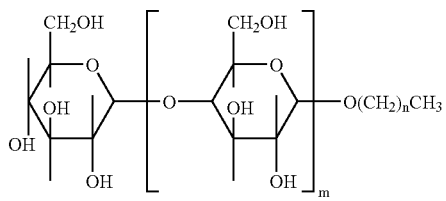

wherein n is an integer between 5 and 19, and m is an integer between 1 and 3.

5. A composition according to claim 4 wherein the surfactant alkyl polysaccharide contains one or more sugar units selected from the group consisting of maltose, arabinose, xylose, mannose, galactose, gulose, idose, talose, allose, altrose, sucrose, fructose, sorbose, levulose, lactose, allulose, tagatose, alloheptulose, sedoheptulose, glucoheptulose, mannoheptulose, guloheptulose, idoheptulose, galactoheptulose, taloheptulose and derivatives thereof.

6. A composition according to claim 2 wherein the salt of chlorhexidine is selected from the group consisting of gluconate, isethionate, formate, acetate, glutamate, succinamate, monoglycolate, dimethanesulfonate, lactate, diisobutyrate and glucoheptonate salts.

7. A composition according to claim 6 wherein the antimicrobial agent is chlorhexidine digluconate.

8. A composition according to claim 7 wherein the amount of chlorhexidine digluconate does not exceed 4.5% w/v.

9. A composition according to claim 2 wherein the chlorophenol derivative is selected from the group consisting of dichlorophene, p-chloro-m-xylenol, chlorophene, o-phenylphenol, and 2,4,4-trichloro-2-hydroxy-diphenylether.

10. A composition according to claim 9 wherein the antimicrobial agent is 2,4,4-trichloro-2-hydroxydiphenylether.

11. A composition according to claim 10 wherein the amount of 2,4,4-trichloro-2-hydroxydiphenylether does not exceed 3% w/v.

12. A composition according to claim 1 wherein the antimicrobial agent has a water solubility of at least 0.001% w/v at ambient temperature.

13. A composition according to claim 1 wherein the alkyl alcohol is a lower alkyl alcohol.

14. A composition according to claim 13 wherein the lower alkyl alcohol is ethanol, isopropanol or n-propanol or a combination thereof.

15. A composition according to claim 13 wherein the lower alkyl alcohol is isopropanol, n-propanol or a combination thereof.

16. A composition according to claim 1 wherein the amount of aryl alcohol does not exceed 3% w/v.

17. A composition according to claim 1 further comprising one or more ingredients selected from the group consisting of
   (a) a solubilising agent,
   (b) a foaming agent,
   (c) one or more viscosity modifiers,
   (d) preservatives,
   (e) other conventional additives, and
   (f) additional surfactants.

18. A composition according to claim 17 wherein the solubilising agent is propylene glycol, a hydrotrope or mixtures thereof.

19. A composition according to claim 18 wherein the hydrotrope is selected from the group consisting of urea, cumenesulfonate, toluenesulfonate, xylenesulphonate and the ethanolamine salts of citric and other hydroxycarboxylic acids.

20. A composition according to claim 17 wherein the foaming agent is an alkylaminooxide, alkylmono or diethanolamide.

21. A composition according to claim 20 wherein the foaming agent is selected from the group consisting of lauryl condensates, cocodiethanolamide condensates, monoethanolamide condensates, lauryl dimethylamine oxides and cetyl dimethylamine oxides, and wherein the viscosity modifier is selected from the group consisting of cellulose derivatives, guar resins and carbopol resins.

22. A composition according to claim 17 wherein the preservative is selected from the group consisting of imidazolidinyl derivatives, urea derivatives, methyl p-hydroxy benzoic esters and propyl p-hydroxy benzoic esters.

23. A composition according to claim 17 wherein the conventional additives are selected from the group consisting of coloring agents, fragrances, antioxidants, emollients, stabilising agents and thickeners.

24. A composition according to claim 23 wherein the thickener is carboxymethylcellulose.

25. A composition according to claim 17 wherein the additional surfactant is selected from the group consisting of amphoteric surfactants, anionic surfactants and nonionic surfactants.

26. A composition according to claim 25 wherein the additional surfactant includes a quaternary ammonium compound or a high foaming anionic surfactant.

27. A composition according to claim 26 wherein high foaming anionic surfactant is selected from the group consisting of laurylethoxysulfonate, a sarcosinate and sodium 2-laurylethersulphate.

28. A composition according to claim 17 wherein additional ingredients are selected to avoid incompatibility with any of the other ingredients of the composition or the antimicrobial agent.

29. A composition according to claim 1 wherein the pH is 8 or less.

30. A composition according to claim 29 wherein the pH is in the range 5 to 7.

31. A composition according to claim 30 wherein the pH is about 5.5.

32. A composition according to claim 1 wherein the pH is controlled to avoid precipitation of ingredients.

33. A composition according to claim 1 wherein the pH is adjusted by an organic acid.

34. A composition according to claim 33 wherein organic acid is selected from the group consisting of lactic acid, acetic acid, citric acid and gluconic acid.

35. A composition according to claim 34 wherein the organic acid is gluconic acid.

36. A method of decontaminating surfaces contaminated with bacteria including the Pseudomonas microorganism, comprising contacting the surface with a disinfectant cleansing composition, said composition comprising an antimicrobial agent; at least 2% w/v of an alkylpolysaccharide surfactant; at least one alkyl alcohol; and at least one aryl alcohol, wherein the total weight of said alkyl and aryl alcohols is at least 55% w/v of the composition.

* * * * *